United States Patent [19]

Hanaway

[11] Patent Number: 4,681,741
[45] Date of Patent: Jul. 21, 1987

[54] REAGENT DISPENSER FOR AN ANALYZING SYSTEM

[75] Inventor: Richard W. Hanaway, Roseville, Calif.

[73] Assignee: American Hospital Supply Corporation, Evanston, Ill.

[21] Appl. No.: 943,820

[22] Filed: Dec. 17, 1986

Related U.S. Application Data

[63] Continuation of Ser. No. 750,791, Jul. 1, 1985, abandoned.

[51] Int. Cl.⁴ .......................... B01L 3/02; B01J 35/00
[52] U.S. Cl. ................................. 422/100; 73/863.32; 73/864.17; 73/864.87; 222/137; 222/144; 222/144.5; 422/63
[58] Field of Search ........... 73/863.31, 863.32, 864.17, 73/864.18, 864.87; 422/63, 64, 67, 100; 222/135, 137, 144, 144.5

[56] References Cited

U.S. PATENT DOCUMENTS

| | | | |
|---|---|---|---|
| RE. 28,801 | 5/1976 | Acker et al. .................... 356/201 |
| 3,074,597 | 1/1963 | Felts .................... 222/144 |
| 3,957,583 | 5/1976 | Gibson et al. .................... 195/103.5 |
| 3,973,696 | 8/1976 | Moore .................... 222/144 |
| 4,096,972 | 6/1978 | Bartels et al. .................... 222/144.5 |
| 4,116,067 | 9/1978 | Pankratz et al. .................. 73/863.31 |
| 4,116,775 | 9/1978 | Charles et al. .................... 195/103.5 |
| 4,118,280 | 10/1978 | Charles et al. .................... 195/127 |
| 4,448,534 | 5/1984 | Wertz et al. .................... 356/435 |
| 4,458,544 | 7/1984 | Gyer et al. .................... 73/864.87 |
| 4,517,160 | 5/1985 | Galle et al. .................... 422/65 |
| 4,528,159 | 7/1985 | Liston .................... 422/100 |

FOREIGN PATENT DOCUMENTS 2131168 6/1984 United Kingdom .................. 422/64

*Primary Examiner*—Michael S. Marcus
*Attorney, Agent, or Firm*—Perman & Green

[57] ABSTRACT

A reagent dispensing assembly for use in an automated specimen analysis system. The assembly comprises a dispensing station and a plurality of reagent supply containers associated therewith. A system is provided for positioning a desired one of the reagent containers at the dispensing station for dispensing a desired amount of reagent. A device acts on the containers at the dispensing station for dispensing the desired amount of reagent. A control system coordinates the movement of the respective reagent containers to the dispensing station and the amount of reagent dispensed within a specimen in a specimen tray.

9 Claims, 18 Drawing Figures

DIAGRAMATIC VIEW

DIAGRAMATIC VIEW

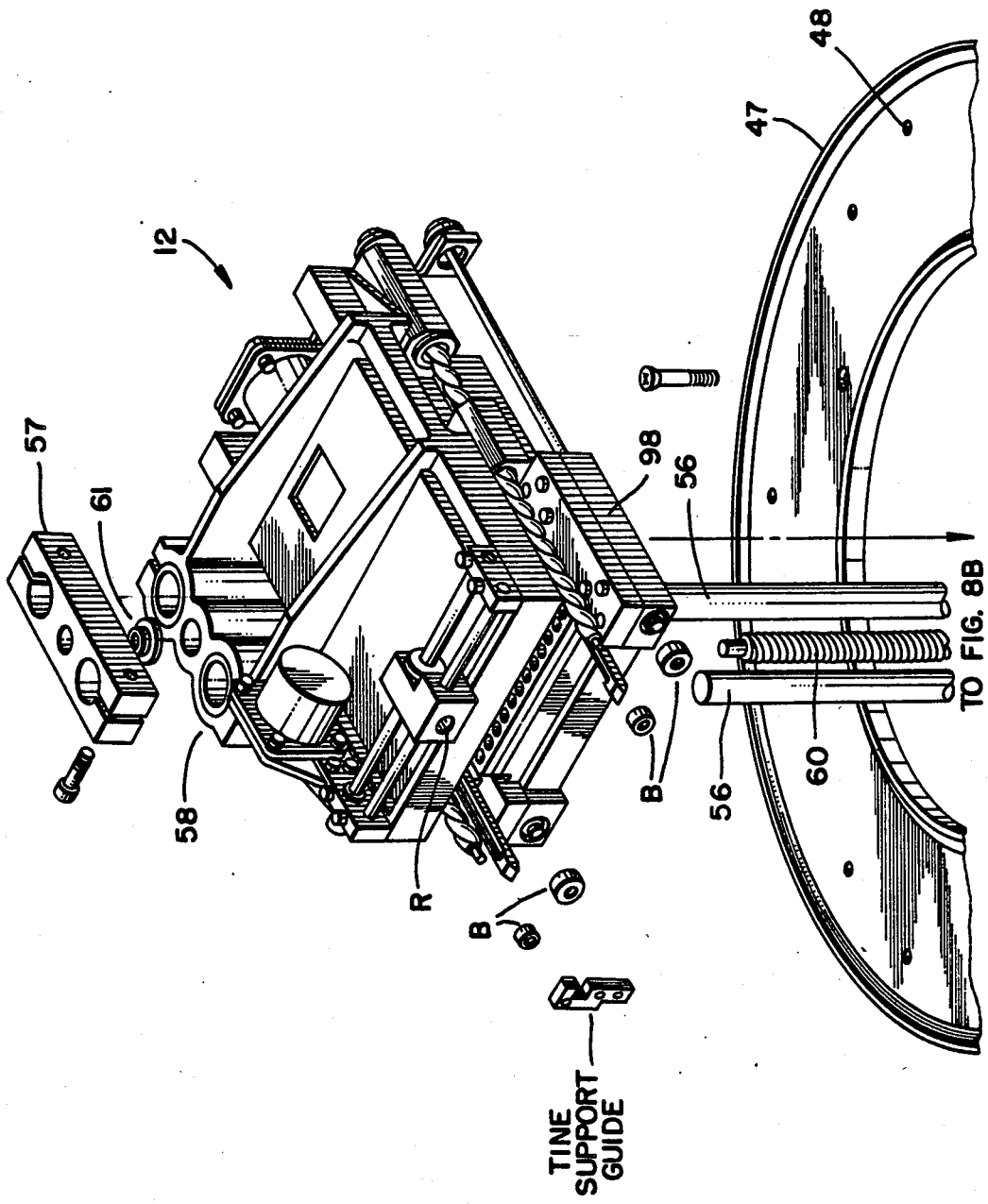

TO FIG. 9B

DIAGRAMATIC VIEW

REAGENT DISPENSER FOR AN ANALYZING SYSTEM

This is a continuation of co-pending application Ser. No. 06/750,791 filed on July 1, 1985 now abandoned.

BACKGROUND OF THE INVENTION

This invention relates to a reagent dispenser apparatus for an automatic specimen analyzing system. Cross reference is made to three other related copending applications assigned to the same assignee: patent application of William P. Armes, Andrew M. Cherniski, Richard W. Hanaway and James C. Hathaway entitled "Automatic Specimen Analyzing System" Ser. No. 750,792 filed July 1, 1985; and my two patent applications entitled "Tower for Analyzing System" Ser. No. 750,793 filed July 1, 1985 and entitled "Tray for Analyzing System" Ser. No. 750,794 filed July 1, 1985.

This invention relates to an automatic specimen analyzing system which substantially reduces operator involvement over presently available systems. After the operator loads the specimen trays into the system of this invention, various operations including incubation after inoculation, adding reagents and analysis of the specimen following incubation are all handled automatically without further operator involvement. A computer-type processor controls the system so that the various operations are carried out in appropriate sequence and the results of the analysis are recorded with specific reference to the sample analyzed.

Automation in microbiology has lagged far behind chemistry and hematology in the clinical laboratory. However, there is presently an intensive effort by industry to develop this field. The best publicized devices for performing automated antimicrobic susceptibility testing use optical detection methods. A continuous flow device for detecting particles 0.5 micron or less has been commercially available since 1970; however, probably due to its great expense, it has no been widely used in the laboratory. Other devices using laser light sources have been suggested but have not proven commercially practicable. Recently, the most attention has been directed to three devices discussed below.

The Pfizer Autobac 1 system (U.S. Pat. No. Re. 28,801) measures relative bacterial growth by light scatter at a fixed 35 degree angle. It includes twelve test chambers and one control chamber in a plastic device that forms multiple contiguous cuvettes. Antibiotics are introduced to the chambers via impregnated paper discs. The antimicrobic sensitivity reader comes with an incubator, shaker, and disc dispenser. Results are expressed as a light scattering index (LSI), and these numbers are related to the Kirby-Bauer "sensitive, intermediate and resistant." MIC measurements which are not available routinely with this instrument. In a comparison with susceptibilities of clinical isolates measured by the Kirby-Bauer method, there was 91% agreement. However, with this system some bacteria strain-drug combinations have been found to produce a resistant Kirby-Bauer zone diameter and at the same time a sensitive LSI.

The Auto Microbic System has been developed by McDonnell-Douglas to perform identification, enumeration and susceptibility studies on nine urinary tract pathogens using a plastic plate containing a $4 \times 5$ array of wells. (See Gibson et al, U.S. Pat. No. 3,957,583; Charles et al, U.S. Pat. No. 4,118,280, and Charles et al, U.S Pat. No. 4,116,775.) The specimen is drawn into the small wells by negative pressure and the instrument monitors the change in optical absorbance and scatter with light-emitting diodes and an array of optical sensors. A mechanical device moves each plate into a sensing slot in a continuous succession so that each plate is scanned at the rate of one an hour, and an onboard digital computer stores the optical data. The system will process either 120 or 240 specimens at a time. One can query the status of each test via a CRT-keyboard console, and hard copy can be made from any display. When the system detects sufficient bacterial growth to permit a valid result, it automatically triggers a print-out. Following identification in four to thirteen hours, a technologist transfers positive cultures to another system which tests for antimicrobic susceptibility. The results are expressed as "R" (resistant) and "S" (susceptible); however, no quantitative MIC data are provided.

It should be noted that Gibson et al, U.S. Pat. No. 3,957,583 do not include automation techniques, but use naked-eye inspection or a manually-operated colorimeter. Scanning is therefore a hand or a mechanical operation. Charles et al, U.S. Pat. Nos. 4,116,775 and 4,118,280 also require mechanical movement of their cassette for reading different rows.

The Abbot MS-2 system consists of chambers composed of eleven contiguous cuvettes. Similar to the Pfizer Autobac 1, the antimicrobial compounds are introduced by way of impregnated paper discs. An inoculum consisting of a suspension of organisms from several colonies is introduced into the culture medium, and the cuvette cartridge is filled with this suspension. The operator inserts the cuvette cartridge into an analysis module which will handle eight cartridges (additional modules can be added to the system). Following agitation of the cartridge, the instrument monitors the growth rate by turbidimetry. When the low growth phase occurs, the system automatically transfers the broth solution to the eleven cuvette chambers; ten of these chambers contain antimicrobial discs while the eleventh is a growth control.

The device performs readings at five minute intervals, and stores the data in a microprocessor. Following a pre-set increase of turbidity of the growth control, the processor establishes a growth rate constant for each chamber. A comparison of the antimicrobic growth rate constant and control growth rate constant forms the basis of susceptibility calculations. The printout presents results as either resistant or susceptible and if intermediate, susceptibility information is expressed as an MIC.

Non-optical methods have also been used or suggested for measuring antimicrobic sensitivity in susceptibility testing. These have included radiorespirometry, electrical impedance, bioluminescence and microcalorimetry. Radiorespirometry, based on the principle that bacteria metabolized carbohydrate and the carbohydrate carbon may be detected following its release as $CO_2$ involves the incorporation of the isotope C– into carbohydrates. Released $C^{14}O_2$ gas is trapped and beta counting techniques are used to detect the isotope.

The major difficulty in applying the isotope detection system to susceptibility testng, however, is that an antimicrobic agent may be able to stop growth of a species of bacteria, yet metabolism of carbohydrate may continue. Less likely, a given drug may turn off the metabolic machinery that metabolizes certain carbohydrates, but growth may continue. This dissociation between metabolism and cell growth emphasizes the fact that measurements for detecting antimicrobic susceptibility should depend upon a determination of cell mass or cell number rather than metabolism.

The electrical impedance system is based on the fact that bacterial cells have a low net charge and higher electrical impedance than the surrounding electrolytic bacterial growth media. A pulse impedance cell-counting device can be used to count the cells; however, available counting devices are not designed to handle batches of samples automatically, and generally do not have the capacity to distinguish between live and dead bacterial cells.

Another approach with electrical impedance has been to monitor the change in the conductivity of the media during the growth phase of bacteria. As bacteria utilize the nutrients, they produce metabolites which have a greater degree of electrical conductance than the native broth so that as metabolism occurs, impedance decreases. However, since this technique measures cell metabolism rather than cell mass, its applicability to antimicrobic susceptibility detection suffers from the same drawback as radiorespirometry.

Bioluminescence has also been suggested for the detection of microorganisms. It is based on the principle that a nearly universal property of living organisms is the storage of energy in the form of high energy phosphates (adenosine triphosphate, ATP), which can be detected through reaction with firefly luciferase. The reaction results in the emission of light energy which can be detected with great sensitivity by electronic light transducers. Although a clinical laboratory may obtain a bioluminescence system to detect the presence of bacteria in urine, the technique is expensive due to the limited availability of firefly luciferase, and problems have been encountered in standardizing the system.

Microcalorimetry is the measurement of minute amounts of heat generated by bacterial metabolism. The principle exhibits certain advantages, but laboratories have not adopted such a system, one serious drawback being that the system measures metabolic activity rather than bacterial mass or number.

In U.S. Application Ser. No. 082,228, filed on Oct. 5, 1979, by Wertz, Hathaway and Cook, now U.S. Pat. No. 4,448,534, granted May 15, 1984, assigned to the assignee of the present invention, an automatic scanning apparatus for performing optical density tests on liquid samples as well as methods for testing for antibiotic susceptibility and identifying microorganisms is disclosed. The apparatus of the prior application includes a system for automatically scanning electronically each well of a multi-well tray containing many liquid samples. A light source, preferably a single source, is passed through the wells to an array of photosensitive cells, one for each well. There is also a calibrating or comparison cell receiving the light. Electronic apparatus read each cell in sequence quickly completing the scan without physical movement of any parts. The resultant signals are compared with the signals from a comparison cell and with other signals or stored data, and determinations are made and displayed or printed out.

A system of the type described in this prior application is sold under the trademarks "MicroScan" and "autoSCAN-3" by the American Scientific Products Division of American Hospital Supply Corporation, McGraw Park, Ill.

A description of the MicroScan System appears in a brochure covering it which was published in 1981.

While the MicroScan System represents a substantial advancement in the automation of microbiological analysis, it still requires operator involvement to handle operations such as incubation, addition of reagents and insertion for the autoscan analysis operation. In other words, for the MicroScan System, presently in use, an operator must perform the operations of placing the tray in a suitable system for incubation for the desired period and after incubation, adding reagents and inserting the tray in the analyzer. In accordance with the present invention, all of these operation after insertion of the tray in the system are carried out fully and automatically.

SUMMARY OF THE INVENTION

In accordance with this invention, a reagent dispenser assembly is provided for use in an automated analysis system. The reagent delivery system in accordance with this invention utilizes a plurality of remote reagent supply containers and a system for selectively dispensing the desired amount of reagent from the corresponding supply container. The system preferably includes a remote dispensing head arranged at a work station for administering the reagents to specimen trays holding a plurality of specimen.

The reagent dispenser assembly of this invention comprises a dispensing station having a plurality of reagent supply containers associated therewith. Means are provided for positioning a desired one of the reagent containers at the dispensing station for dispensing a desired amount of reagent therefrom and means are provided for acting on the desired one of the containers for dispensing the desired amount of reagent. Preferably, the positioning means comprises a reagent container support carousel arranged to rotate the containers past the dispensing station which is arranged tangentially of the carousel. Preferably, a means is provided for releasably securing the containers to the carousel.

Preferably, the reagent containers comprise syringes and the means acting on the containers to dispense the desired amount of reagent comprises an anvil for engaging a plunger of the desired one of the syringes. The anvil is arranged for movement longitudinally of the desired one of the syringes. Means are provided for driving the anvil to move it selectively between a first home position where it does not engage the syringe, a second dispense start position where it first engages the plunger and a third finish position where it pushes the plunger in order to dispense the desired amount of reagent.

Preferably, a control system is provided for coordinating the movement of the dispense carousel to position the desired one of the syringes at the dispensing station and coordinate the movement of the anvil between its respective position to dispense the desired amount of reagent. Preferably, the control means includes means for sensing the first engagement between the anvil and the plunger and responsive thereto means for closing the anvil to move to its third position.

Preferably a dispense head is arranged remotely from the dispenser assembly. The dispense head is arranged to administer the reagent to a desired specimen in the specimen tray. A suitable conduit is used to connect the dispense head to the dispenser assembly.

It is an aim of this invention to provide a regent dispenser assembly for use with an automated specimen analysis system wherein the dispenser assembly is adapted to selectively administer one of a plurality of reagents contained therein.

It is a further aim of this invention to provide a dispenser assembly as above wherein a control system coordinates a movement of respective reagent containers to a dispensing station and the amount of reagent dispensed by a remote dispense head.

These and other aims will become more apparent from the following description and drawings.

BRIEF DESCRIPTION OF THE DRAWINGS

FIG. 8A–8B are exploded views of the carousel and scanning assembly of this invention.

DETAILED DESCRIPTION OF THE PREFERRED EMBODIMENTS

Figure 1:
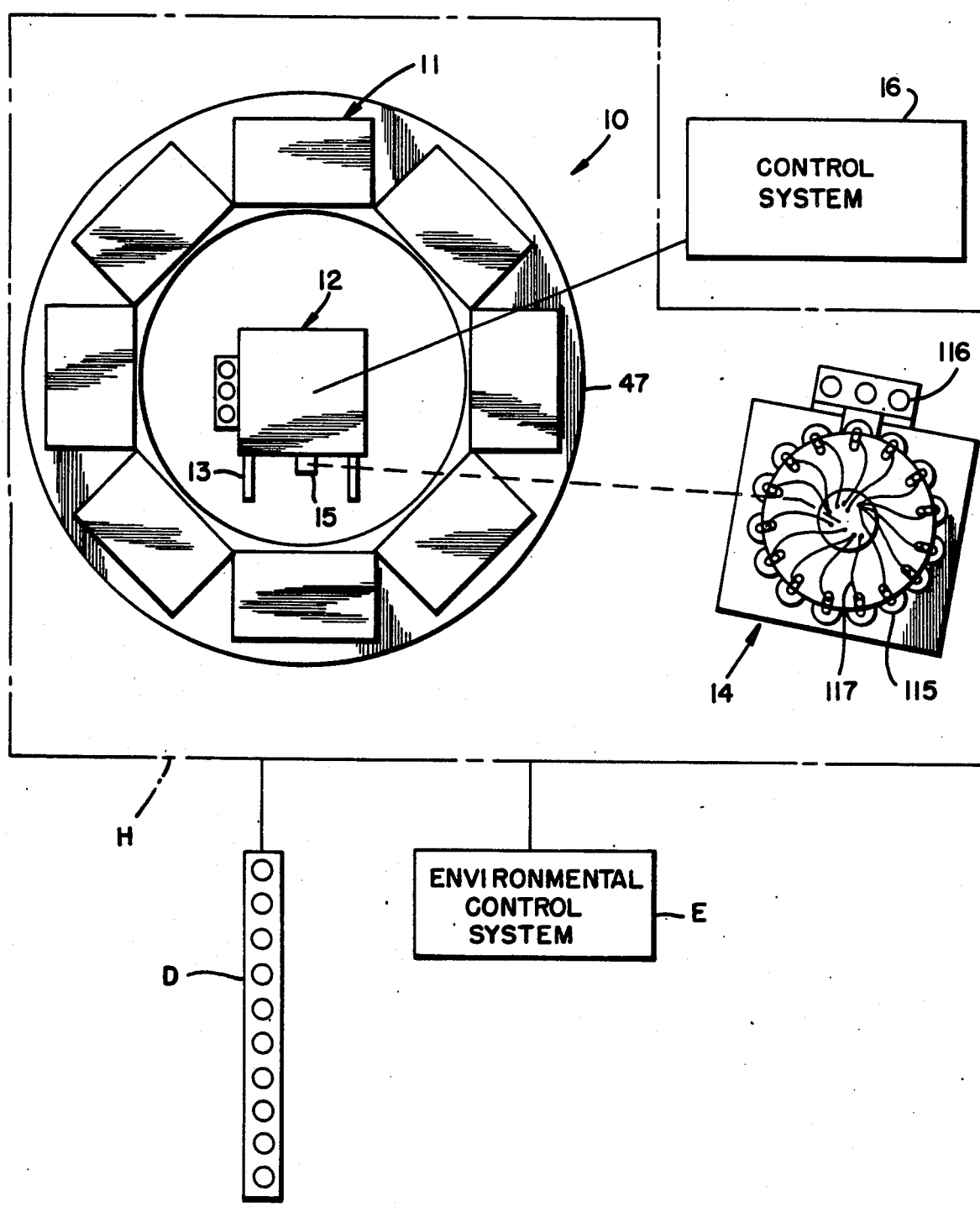
FIG. 1 is a schematic representation of an automatic specimen analyzing system in accordance with this invention.
Figure 2:
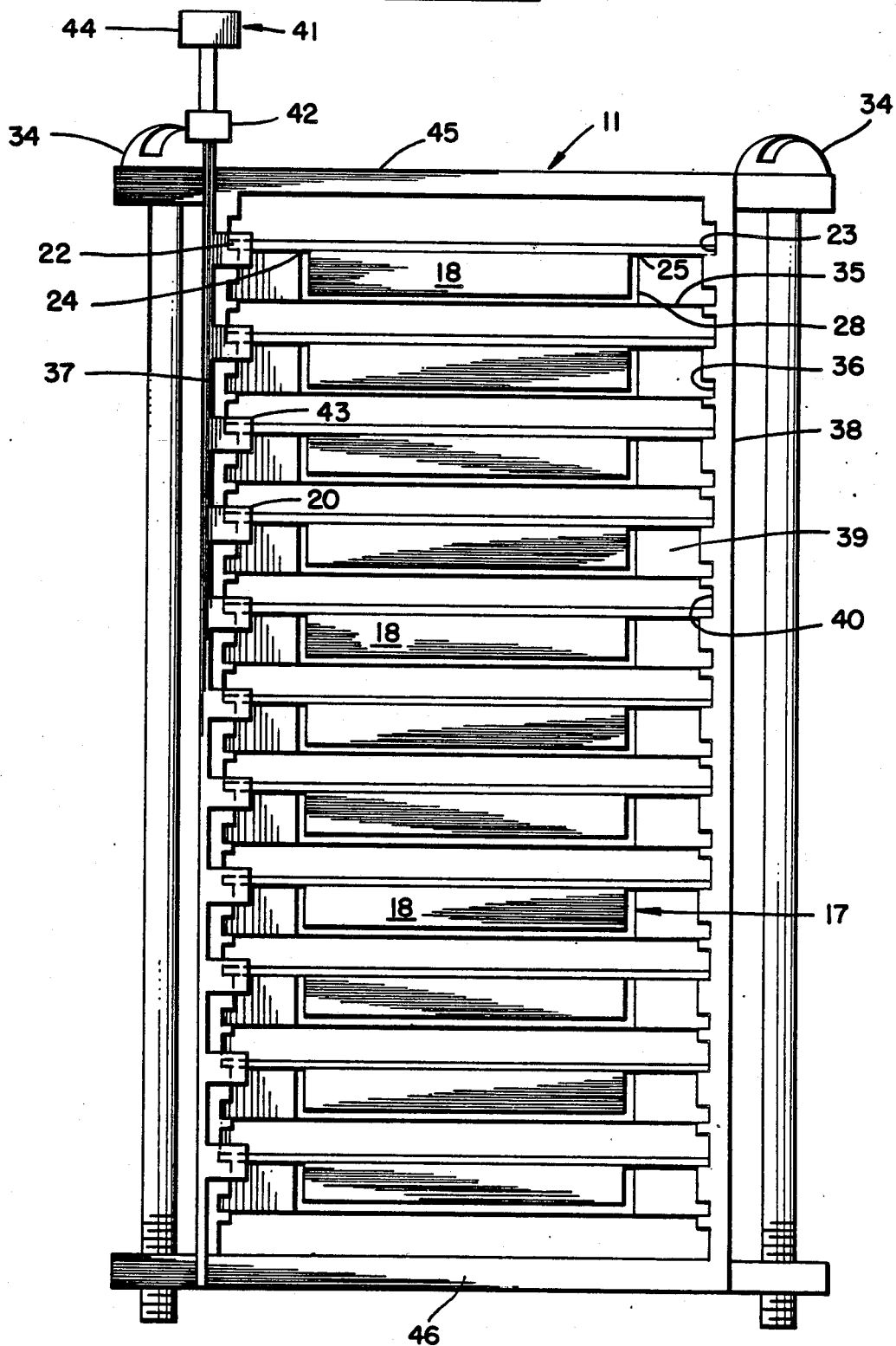
FIG. 2 is a schematic representation of a tray tower of the type used in the apparatus of FIG. 1.

Referring now to FIG. 1, an automatic specimen analyzing system 10 is shown schematically. The system 10 is adapted to analyze biologic specimens which have been selectively treated as desired. The specimens are arranged in specimen trays wherein each tray contains a plurality of the specimens. The system 10 is adapted to automatically carry out, after the operator loads the specimen trays into the system 10, operations such as addition of reagents, incubation and the analysis.

The specimen trays are loaded by the operator into a plurality of specimen tray supporting towers 11. The exact number of towers utilized in the system may be set as desired. However, the system is particularly adapted for use with a plurality of such towers 11. A work station 12 is arranged in association with the tray towers 11 for selectively treating or analyzing the specimens in the trays supported by the towers 11. A selectively operable tray moving means 13 is supported at the work station and serves to remove a specimen tray from the tray support tower and move it to the work station 12. The tray moving means 13 also serves to reinsert the tray into the tray supporting tower 11. A reagent delivery system 14 includes a remote dispensing head 15 connected thereto and supported by the work station 12. The reagent delivery system 14 is selectively operable to administer a desired amount of at least one reagent to desired ones of the specimens in the tray through the remote dispensing head 15.

A housing H preferably surrounds and encloses the environmentally sensitive elements of the automatic scanning analyzing system 10. Those elements include the tray support towers 11, the work station, the tray moving means 13, the reagent delivery means 14 and the remote dispensing means 15. Although these components can be used in a controlled environmental room without a housing, it is intended that the automatic specimen analyzing 10 of this invention includes such a housing for controlling temperature and humidity to provide proper incubation of the specimen.

The environmental control system E is connected to the housing H for controlling the temperature and humidity within the housing. The environmental control system comprises conventional means for controlling the humidity and temperature of the atmosphere within the housing H. While it is preferred for the housing H to enclose both the work stations and tray tower area and the remote dispensing area, if desired, the housing may enclose only the work station and tray tower area.

The housing is provided with one or more access doors (not shown) to enable the operator to remove tray tower 11 from the analyzing system 10. For maintenance purposes, the housing may be made removable from the system entirely. If desired, the control system 16 may be built into the housing and the housing H may include an indicator panel such as LED panel D. If desired, vaiours other gages and indicators can be mounted to the housing H.

The work station 12 also includes an analyzing means for determining at least one optical property of desired ones of the specimens in the tray. A control means 16 is adapted to sequentially actuate the tray moving means 13 so that each of the trays are at least sequentially moved to the work station 12 for administration of the reagent by the reagent delivery system 14, then return to the tray support tower 11 and held there for a desired incubation time. Thereafter, the control means again causes the tray to be removed from the tray tower 11 and returned to the work station for analysis. The control means then causes the tray moving means to return the tray to the tray support tower 11 from which it can be removed by the operator for storage or disposal.

Figure 3:
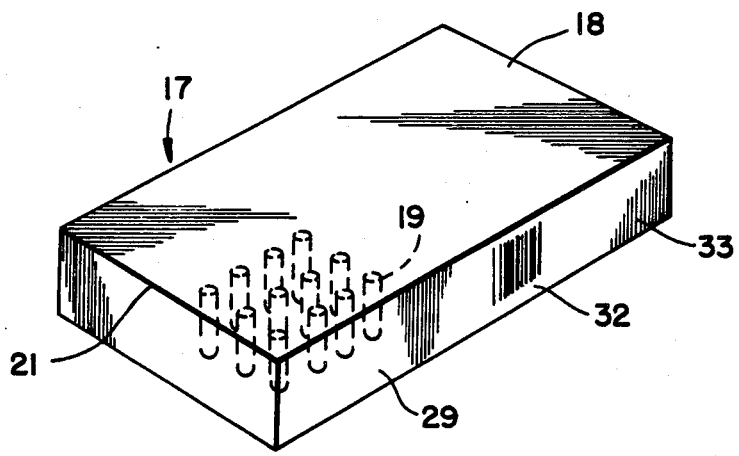
FIG. 3 is a schematic perspective view of a specimen container tray which can be employed in the apparatus of FIG. 1.
Figure 4:
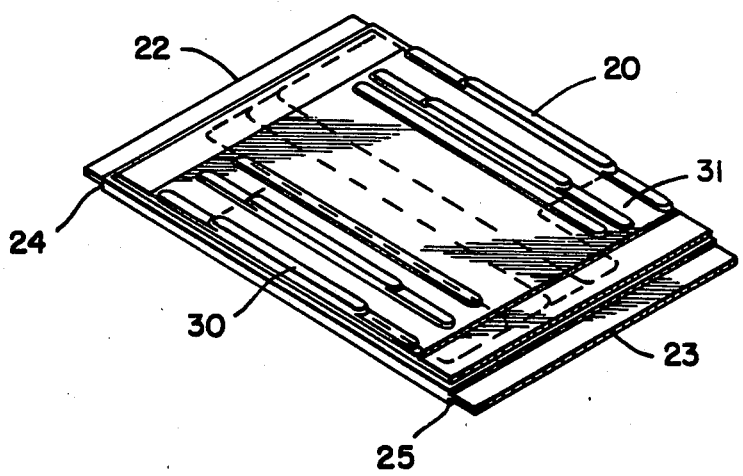
FIG. 4 is a perspective view of a cover member for use with the specimen container tray of FIG. 3.

While the specimen tray itself has not been shown in FIG. 1, it will now be described in detail by reference to FIGS. 2–5. The specimen tray assembly 17 comprises an assembly which is adapted for use in the automatic system 10 for analyzing the specimens. Each tray assembly 17 is adapted to contain a plurality of separate specimens. The tray assembly 17 is comprised of a container tray 18 having a plurality of microcuvettes 19 arranged in a spaced apart grid-like pattern. The container tray 18 is best shown in FIG. 3 and corresponds to the MicroScan specimen panels as described in the background of this application. A cover member 20 is adapted to seat over a top surface 21 of the container tray 18. The cover member 20 is clearly illustrated by reference to the aforenoted FIGS. 2, 4 and 5. The cover member 20 includes tab portions 22 and 23 which extend outwardly in the plane of the cover members 20 from first and opposing edges 24 and 25 of the member. The tab portions 22 and 23 are adapted, when the tray assembly 17 is inserted in the tray tower 11, to control the movement of the cover member 20 so that the container tray 18 can be readily removed from the tray tower 11 without the cover member. The cover member is left in the tray tower so that the aforenoted operations of reagent additions or analysis can be readily carried out on the specimens in the container tray 18.

Figure 5:
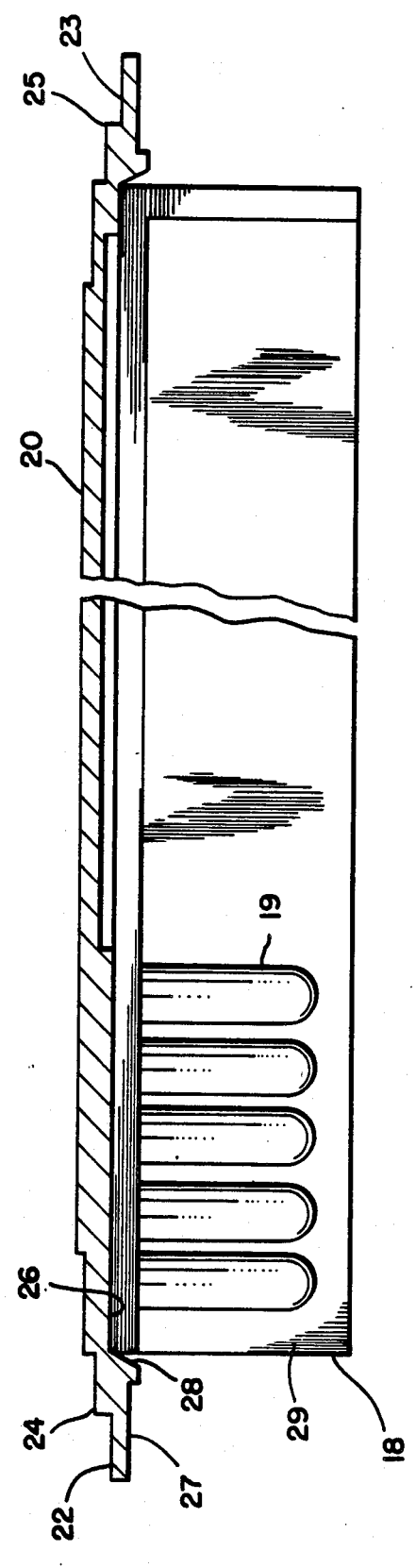
FIG. 5 is a cross-section of a specimen tray in accordance with this invention comprising a tray container as in FIG. 3 and a cover member as in FIG. 5.
Figure 6:
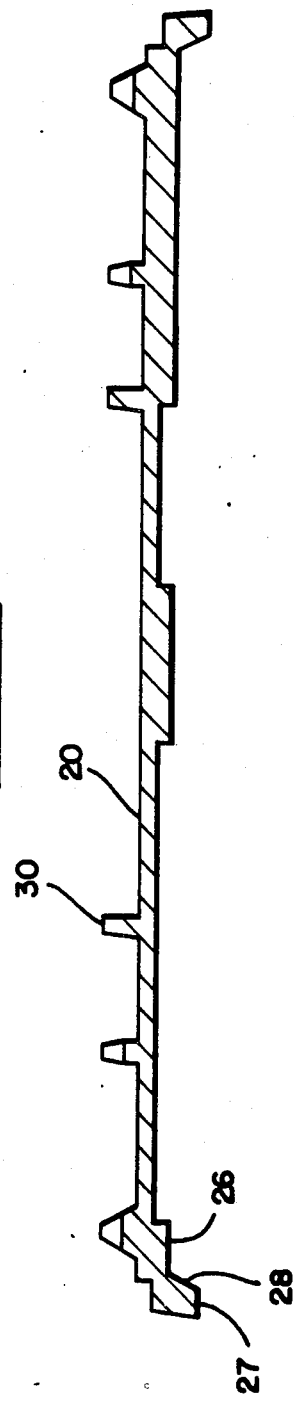
FIG. 6 is a cross-section of a cover member of FIG. 5 taken normal to the direction of the cross-section in FIG. 5.

The cover member also includes means for automatically centering the container tray relative to the cover member 20 to provide proper seating of the cover member on the container tray. With reference to FIG. 5, the centering means preferably comprises a recess 26 in a bottom face 27 of the cover member 20 having a first peripheral wall 28. The first peripheral wall 28 is adapted to seat about a second peripheral wall 29 of the container tray 18. The centering action is provided by inclining the first peripheral wall 28 in the cover member inwardly of its periphery so that when the cover member 20 is urged against a misaligned container tray 18, the inclined first peripheral wall 28 acts on the second peripheral wall 29 of the container tray 18 to center and align the container tray with respect to the cover member. This centering feature of the tray assembly of the present invention plays an important role with respect to the proper removal and reinsertion of the container tray 18 into the tray tower 11. This function will be described in greater detail hereinafter. Proper seating of the cover member 20 over the container tray 18 is important in order to insure that there is no undue evaporation of the contents of the cuvettes 19 in the container tray 18.

The cover member 20 preferably includes stiffening ribs 30 arranged as shown generally parallel to one another along a top face 31 of the cover member 20 and extending longitudinally between the respective tab portions 22 and 23. A plurality of such stiffening ribs 30 are utilized in order to strengthen the cover member so that it can be resiliently urged against the container tray 18 to provide effective sealing against evaporation as will be described in greater detail hereinafter. The stiffening ribs 30 therefore prevent bowing of the cover member 20. It is preferred to avoid such bowing of the cover member 20 in order to reduce evaporation and prevent interference with the container tray 18 as it is removed from the tray tower 11.

In accordance with a preferred embodiment of the present invention, each container tray 18 includes ninety-six cuvettes or wells 19. Further, each container trayy 18, as shown in FIG. 3, can be recognized and identified by a bar code 32 which is provided on a side wall 33 of the container tray which will face the remote dispensing head 15. The bar code is added to the container tray 18 at the time of placing particular samples or specimens in the tray into the control system 16, and have the information associated with each tray represented thereon. The control system preferably comprises a programmable computer which can print out the desired bar code at the time the information is in the system.

Referring again to FIG. 2, it is apparent that the tray support tower 11 is adapted to support a plurality of tray assemblies 17. The exact number of tray assemblies 17 may be set as described. Each tray tower 11 is readily removable from the automatic specimen analyzing system 10 by loosening tie down bolts 34. This allows the tray tower 11 to be releasably connected to the automatic specimen analyzing system.

Each tray assembly 17 rests upon a shelf 35 which is slidingly supported so that it is removable in a first slot 36 in each of a first sidewall 37 and a second side wall 38 of the tray tower. The slots 36 extend in a spaced apart, generally parallel, manner from a first open face 39 in the plane of the drawing to a second open face (not shown) behind the first open face 39. The slots are closed at an end adjacent one of the open faces as will be described in greater detail hereinafter. Each of the shelves 35 is removably supported in the first slots in each of the first and second side walls 37 and 38 to provide a spaced apart parallel and overlapping array of shelves 35 with the spaces between the shelves being adapted to receive the specimen tray assemblies 17.

A corresponding plurality of second slots 40 in each of the first and second side walls 37 and 38 extend in a spaced apart, generally parallel, manner from the first open face 39 to the second face (not shown). The second slots are closed at an end adjacent one of the open faces which is selected to be the same faces as for the first slots 36. The second slots 40 are adapted to receive the cover members 20 and to provide support for movement of the cover member 20 upwardly or downwardly within the width of the slot W. The width W is selected to permit the cover member 20 to move widthwise of the slot as will be described in greater detail hereinafter.

Preferably, selectively operable means 41 are provided at one of the open faces 39 of at least one side wall 37 for partially blocking the open face to prevent the tray assemblies 17 loaded in the tray tower from being pushed out of the opening in that face. The selectively operable means 41 preferably comprises a multi-tabbed member 42 which is slidingly mounted on an edge of the side wall 37 by any suitable means (not shown). The tab member may be moved up and down so that the tray assembly 17 can be inserted or removed from the tower 11 or locked in place. The tabs 43 of the member 42 serve to interfere with the cover member 20 when it is desired to lock the tray assembly 17 in place or to allow free passage of the cover member when the member 42 is moved upwardly out of blocking position. This movement may be accomplished manually by operator intervention or automatically through the use of a suitable solenoid 44 which is controlled by the programmable control system 16.

The tie-down bolts 34 are supported by the respective side walls 37 and 38 of the tower 11 and these, with a top portion 45 and bottom portion 46, comprise a tray tower frame. The tie-down bolts 34 are adapted to screw into a tray tower moving carousel 47 as illustrated in FIG. 1.

If it is desired to sterilize the tray tower, the specimen tray assemblies 17 are removed from the tower. The shelves 35 can also be removed from the tower and sterilized if desired. The tower itself which comprises essentially the frame comprising top and bottom portions 45 and 46 and side walls 37 and 38, can then be sterilized also.

Figure 7:
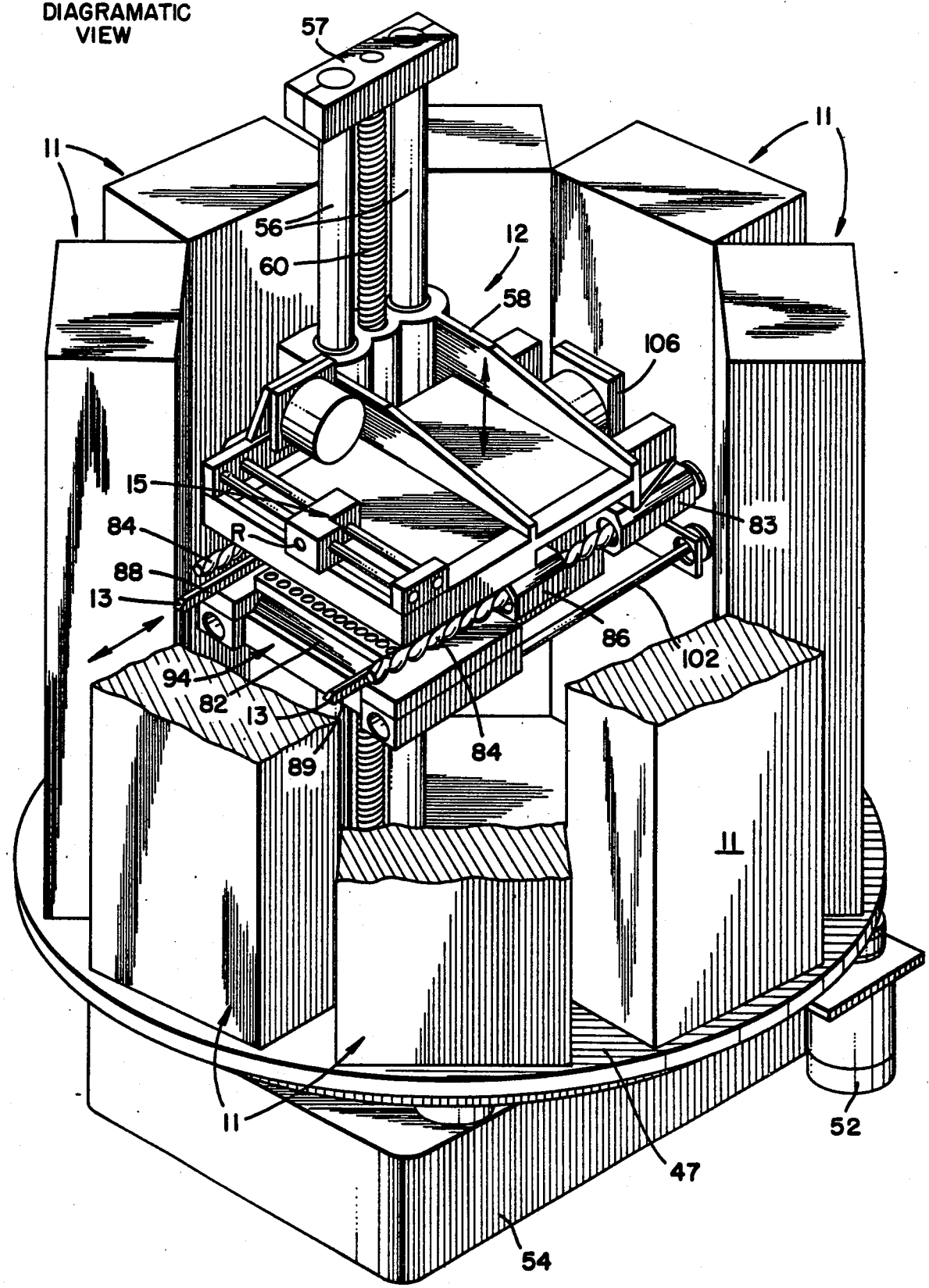
FIG. 7 is a schematic perspective view of the carousel and scanning assembly in accordance with this invention.
Figure 8B:
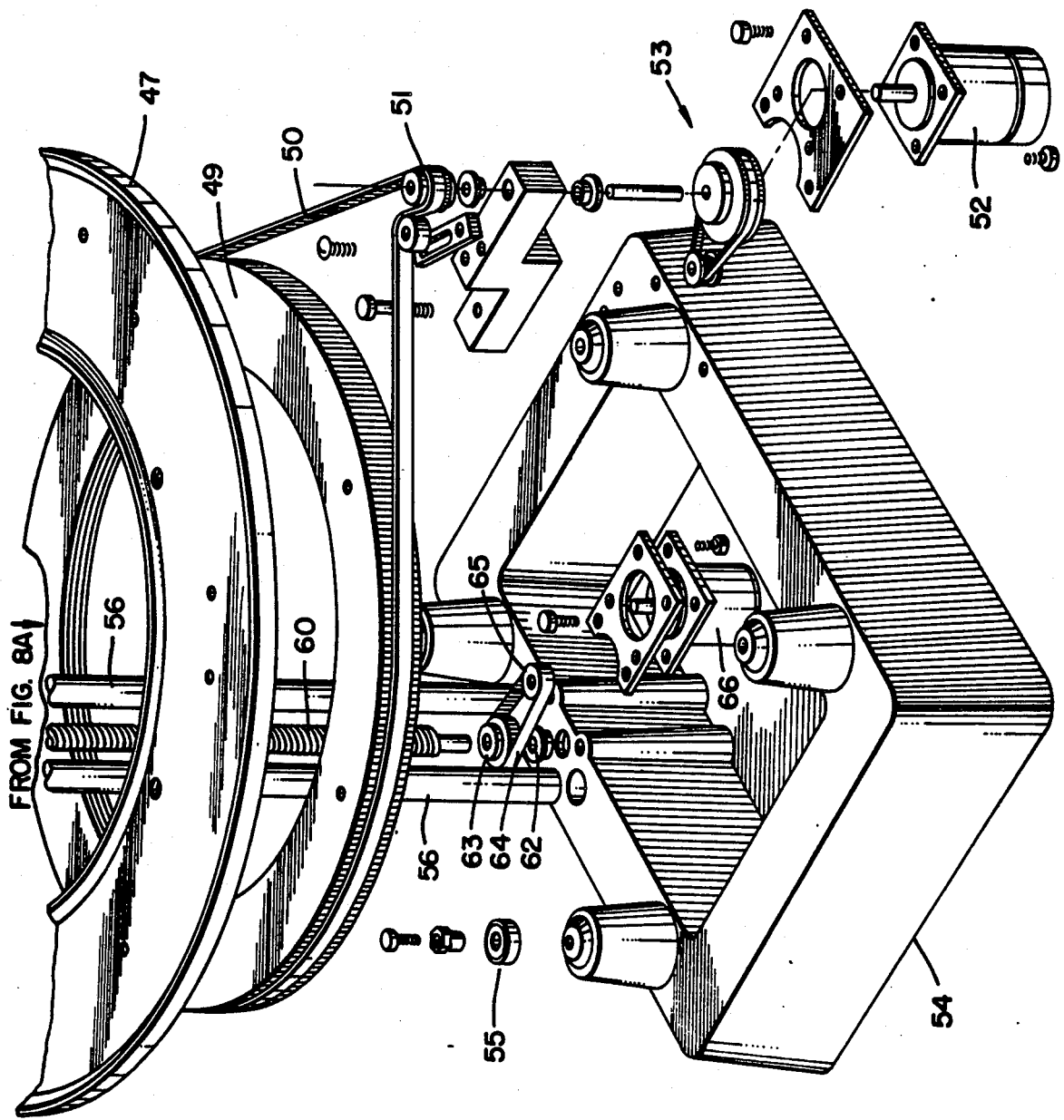
Figure 9A:
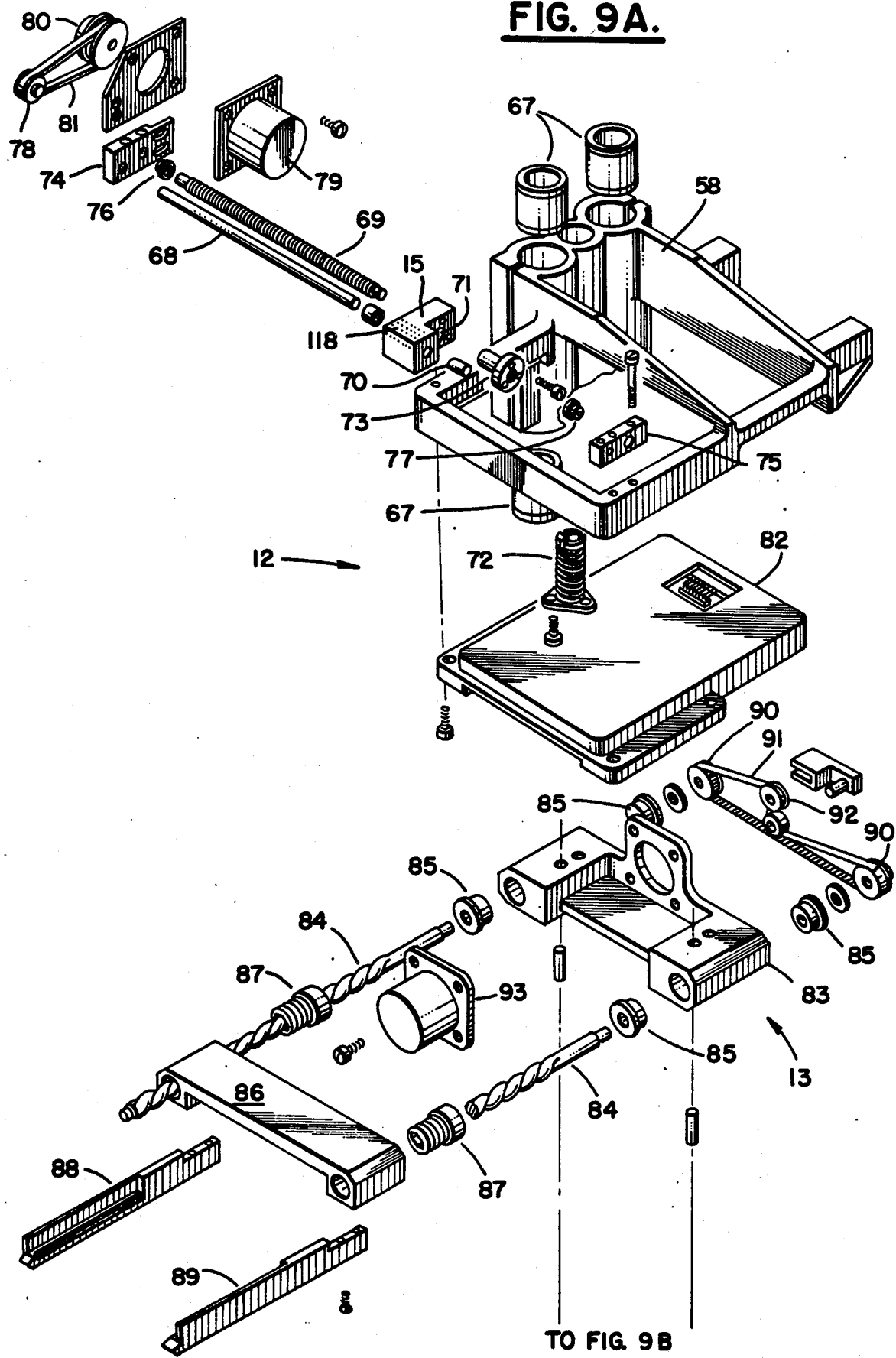
FIG. 9A–9B are more detailed exploded views of the scanning system in accordance with this invention.
Figure 9B:
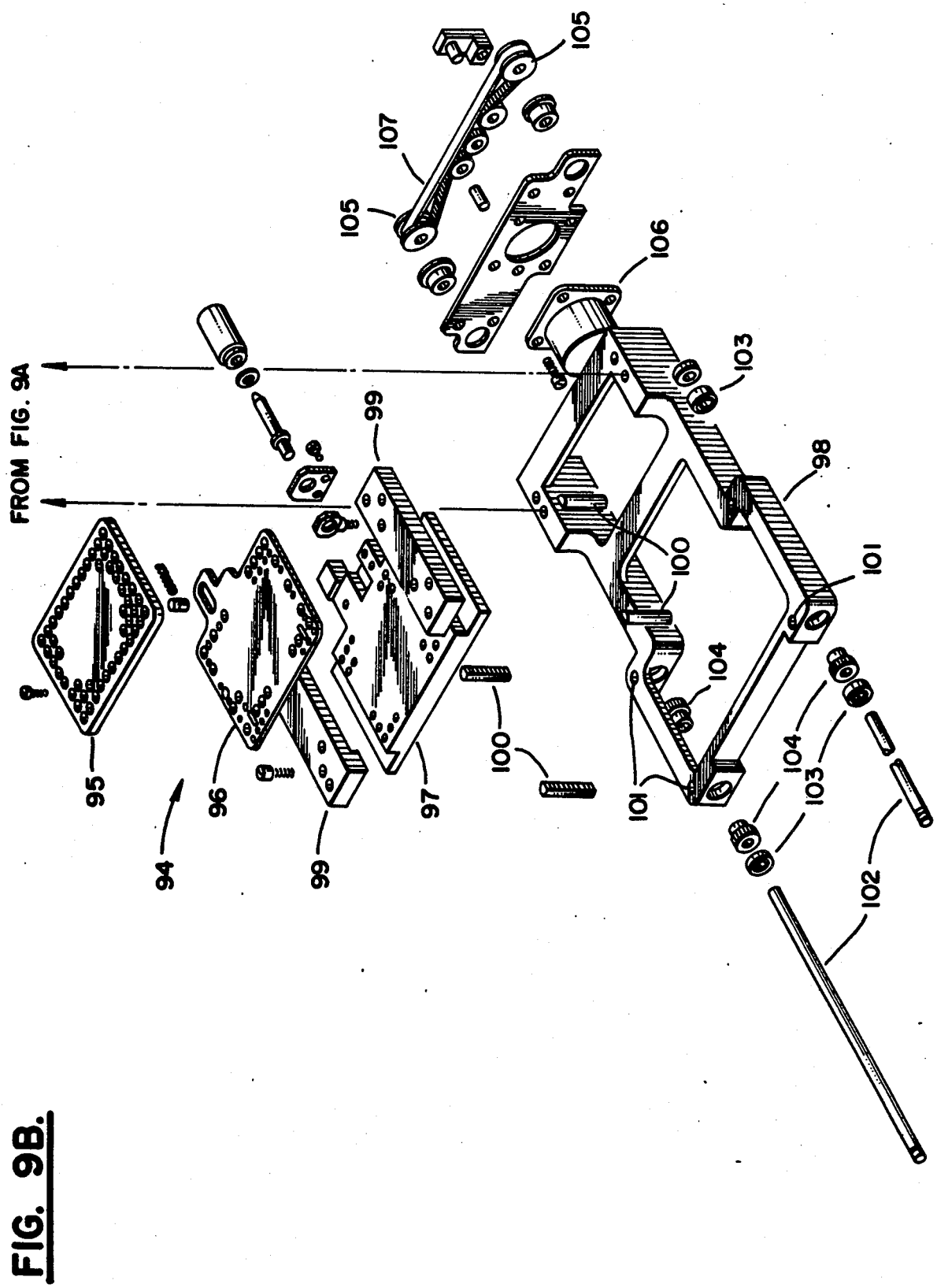

Referring now to FIGS. 7-9, further details of the automatic specimen analyzing system 10 will be provided. In particular, these figures show the various apparatus for moving the tray towers 11 selectively into operative position with respect to the work station, the various elements of the tray assembly moving system and the work station itself. It is desirable to employ a plurality of tray towers 11 which are arranged on a tray tower moving system or carousel 47. The carousel 47 comprises a donut-shaped plate which surrounds the work station 12. Holes 48 are provided in the top surface of the carousel 47. These holes are tapped so that the tie down bolts 34 of a respective tray tower 11 can be screwed therein in order to mount the tray tower to the carousel 47. The tray towers are not shown in FIGS. 8 and 9 in order to better illustrate the other aspects of the automatic specimen analyzing system 10.

A carousel drive pulley 49 is driven by means of a cogged belt 50 arranged about the drive pulley 49 and a cogged pulley 51. A stepping motor 52 drives the cogged pulley 51 via a stepped-down cogged pulley and belt arrangement 53. The actuation of the stepping motor is controlled by the control system 16 and serves to rotate the carousel 47 to position a desired tray tower in operative association with the work station 12. The carousel 47 is rotatably supported on a base frame 54 by means of V-track bearings 55. If desired, however, any appropriate means for rotatably supporting the carousel 47 could be employed. Similarly, any desired drive arrangement could be employed which is adapted to selectively position a desired one of the tray towers in operative association with the work station 12.

A pair of vertical shafts 56 support the work station 12 for vertical movement up and down along the shaft 56 axes. The shafts 56 are supported in the frame 54 and at their opposing ends by a shaft mount 57. A work station carrier frame 58 includes holes 59 with suitable bushings or bearings to provide for sliding movement of the carrier frame 58 along the shafts 56. A vertical axis drive screw 60 is provided to drive the carrier frame 58, supporting the work station 12, up and down vertically along the shafts 56. The drive screw 60 is journaled for rotation in the shaft mount 57 by means of ball bearings 61 and is also journaled for rotation in the frame 54 by means of bearings 62. The portions of the drive screw 60 which are journaled through rotation do not include threads. In addition, the lower portion which is journaled in the base frame 54 includes a drive cogged pulley 63 which is driven by means of a cogged belt 64 and pulley 65 mounted to the shaft of a stepping motor 66. The drive cogged pulley 63 is of a larger diameter than the pulley 65 to provide a step-down drive arrangement. The stepper motor 66 is controlled by the control system 16 to advance the work station 12 up and down as required to carry out the operations of the automatic specimen analyzing system which will be described hereinafter.

Referring now, more particularly, to FIG. 9, the details of the work station itself will be described. The work station carrier frame 58 as previously described is arranged for movement along the shafts 56 by means of linear bearings 67. The remote dispensing head 15 is arranged for movement in a plane normal to the plane of movement provided by the shafts 56 and drive screw 60. This is accomplished by means of a guide rod 68 and dispensing head drive screw 69. The dispensing head 15 is arranged for sliding movement on the rod 68 by means of oilless bearings 70. The drive screw 69 is threaded through a hole 71 so as to provide the desired movement of the dispensing head 15 from side-to-side relative to the carrier frame 58. Preferably, anti-backlash nuts 72 and 73 are employed with respect to drive screws 60 and 69.

The drive screw 69 is journaled for rotation in end support blocks 74 and 75 which, in turn, are mounted to the carrier frame 58. The drive screw is journaled for rotation in the end blocks 74 and 75 by means of bearings 76 and 77. A cogged drive pulley 78 is secured to one end of the drive screw 69. A stepper motor 79 mounted to the carrier frame 58 drives the drive screw 69 by means of a cogged pulley 80 and belt 81. The cogged pulley 80 is relatively larger in diameter than the drive pulley 78, thereby providing a step-up in the drive arrangement.

A photodiode reader card assembly 82 is supported on the underside of the carrier frame 58. This reader card assembly 82 serves in the analysis function of the work station to determine an optical property of the specimens in the tray assembly 17.

An important element of the present automatic specimen analyzing system 10 is a selectively operable tray moving system 13 which serves to remove a tray container 18 from the tray tower and move it into the work station for dispensing reagents into the specimens or their analysis, and for moving the tray container 18 back into the tray tower 11 as required. The tray moving system 13 is supported by the carrier frame 58 and comprises a tray drive mount 83 which is secured to the carrier frame 58. The mount 83 supports therein two parallel spaced-apart helical drive screws 84 which are journaled for rotation in the mount by means of bearings 85. The tray drive mount 83 is located at one end of drive screws 84.

A moving carriage or tray pick-up body 86 is drivingly supported about the drive screws 84 by means of anti-backlash nut assemblies 87. The carriage 86 supports two parallel spaced apart tray pick-up tines 88 and 89. At the opposing ends of the drive screws, drive pulleys 90 are mounted which are driven by means of a cogged belt 91 through cogged pulley 92 which, in turn, is driven by stepper motor 93. The stepper motor 93 is controlled by the control system 16 so as to advance or retract the tines 88 and 89 to respectively move a container tray 18 to and fro in a plane normal to the plane of movement of the carrier frame 58 and in a direction normal to the direction of movement of the remote dispensing head 15.

Supported above and below the tray moving means is the specimen analyzing system or scanning system 94 and 82 comprising a tray block 95, an aperture plate 96, fiber bundle block 97 and photodiode reader card 82. The specimen analyzing system 94 and 82 is essentially the same as that employed commercially in the MicroScan system described in the background of this application. The tray block 95, the aperture plate 96 and the fiber bundle block 97 are arranged for movement vertically to and fro in the same direction as the carrier frame 58, however, in respect to the carrier frame 58. The aforenoted elements are mounted to an optics block frame 98 via optics mounts 99.

The tray block 95, the fiber bundle block 97 and the aperture 96 are arranged for vertical movement on the optics block frame 98 by means of gear racks 100 which are spring-loaded against mounts 99. Mounts 99 are located by two tooling balls and one locating button through three position posts. The three position posts are bolted to frame 98. Gear racks 100 are slidingly supported in holes 101 in the optics block frame 98. Shafts 102 are journaled for rotation in the frame 98 by means of bearings 103. Drive gears 104, in respective alignment with the gear racks 100, are supported on shafts 102 whose axes are arranged normal to the direction of movement of the gear rack 100. Cogged pulleys 105 are supported at one end of the shafts 102 to provide drive to the shafts. The pulleys 105 are driven by means of a stepper motor 106 and a cogged belt 107. The stepper motor 106 is controlled by the control system 16 to provide clockwise or counterclockwise rotation of the shafts 102 in order to advance the gear racks 100 up or down and thereby advance the specimen analyzing system 94 up and down into and out of engagement with the bottom of a respective container tray 18 arranged at the work station 12.

While a carousel-type arrangement is shown for moving the respective tray tower 11 into operative association with the work station 12, any desired moving means could be employed including various belt-type arrangements. As previously described, the tray towers 11 comprise generally rectangular frames having a plurality of tray support shelves 35 removably supported therein.

Referring to the FIGS. 10–14, tower 11, preferably, also includes means 108 for biasing the cover member 20 against the container tray 18 when they are positioned in the tower. The biasing means 108 and the operation of the tray moving system 13 and work station 12 will now be illustrated by considering FIGS. 10–14.

Figure 10:
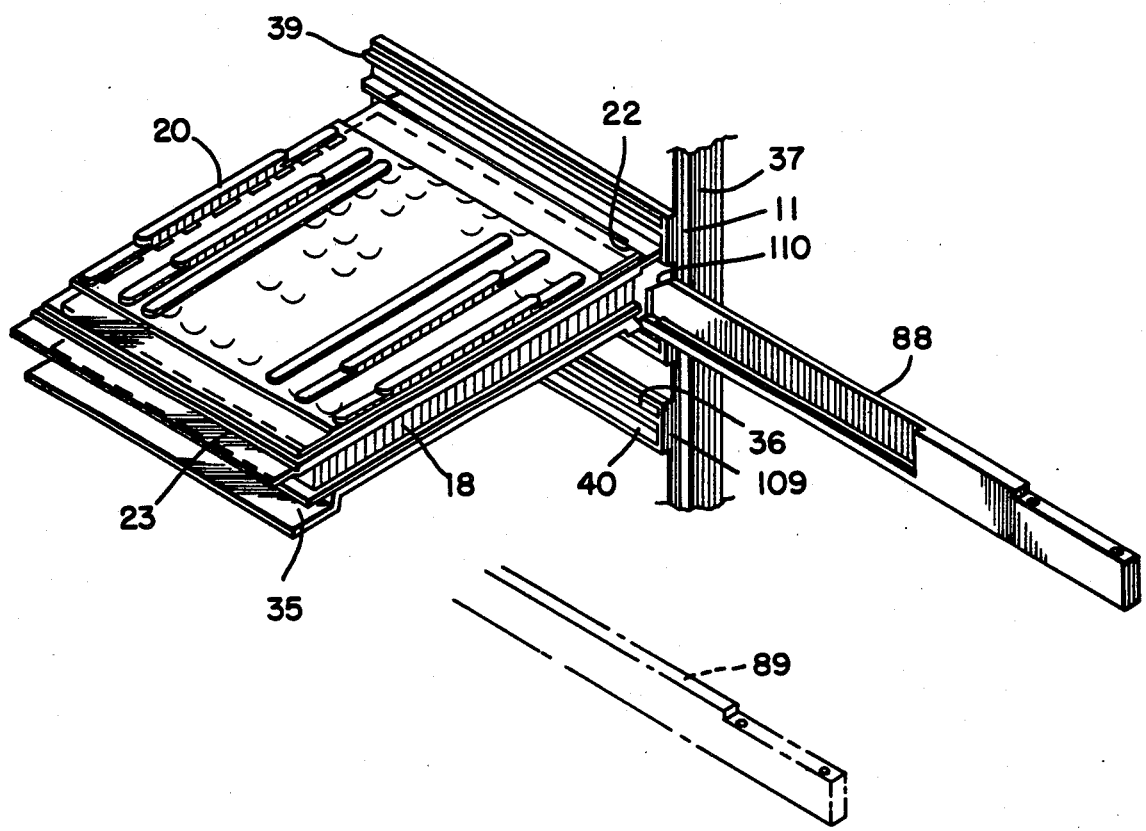
FIG. 10 is a partial perspective view illustrating operation of the tray moving system of this invention.
Figure 11:
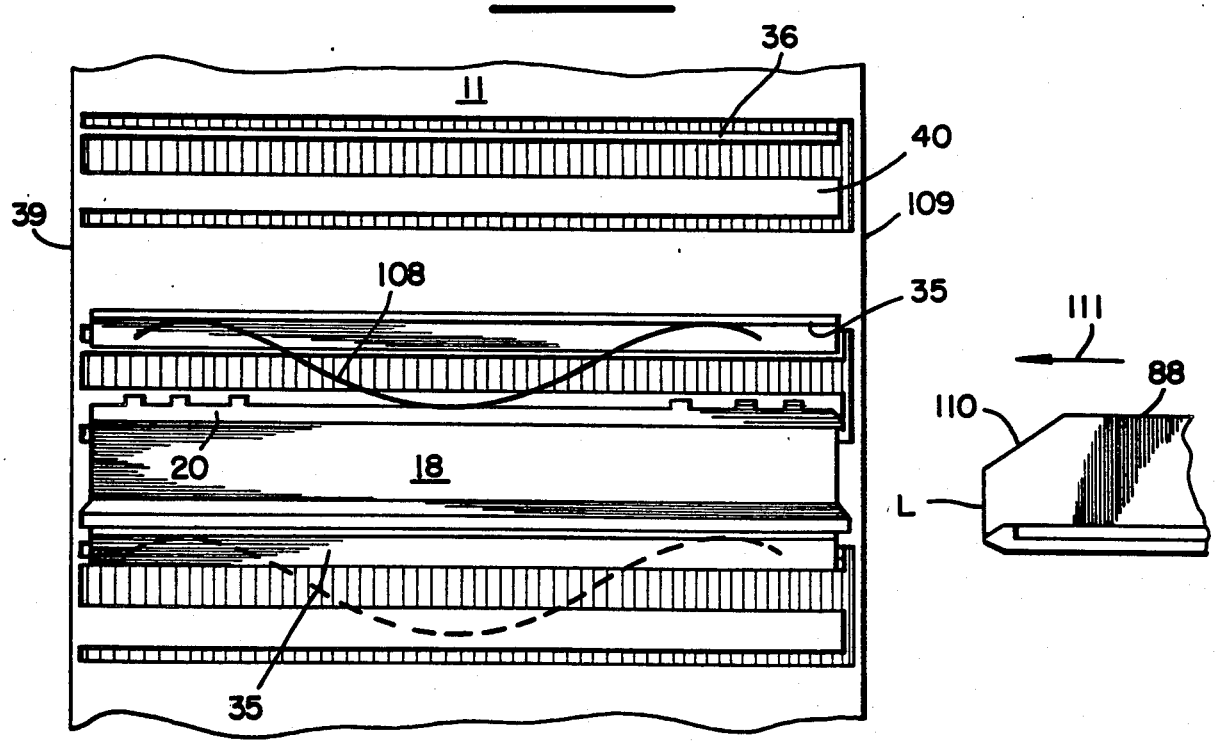
FIG. 11 is a partial side view in partial cross-section, illustrating the operation of the tray moving system of this invention.
Figure 12:
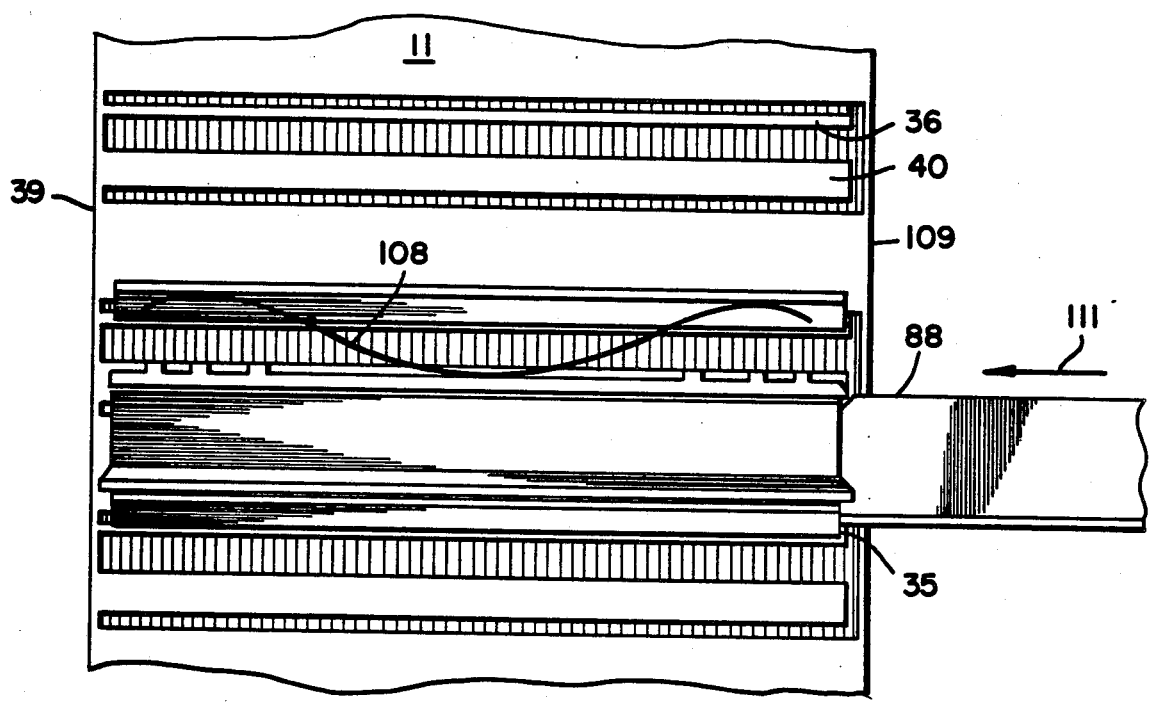
FIG. 12 is a partial side view as in FIG. 11 at a later stage in the tray moving operation.

As shown in FIG. 10, the tray tower 11 includes side wall 37 having respective slots 36 and 40 ae previously described. A tray shelf 35 is supported in the slot 36 whereas the cover member 20 is held captive by the tray tower second slot 40. It is held captive because the second slot 40 is closed at its end at open space 109. Similarly, the tray shelf 35 is captured by the closed end of the slot 36 at the open space 109. The tray tines 88 and 89 include at their leading edges an inclined surface 110 which serves to engage the tab portions 22 or 23 to raise the cover member 20 off of the container tray 18 as the tines proceed into the tray tower by means of the drive imparted by stepper motor 93. A resilient biasing means, as shown in FIG. 11, comprises a compression spring 108 which is supported by the bottom of the next above shelf 35. The purpose of the biasing means or spring 108 is to ensure engagement sealingly as possible between the cover member 20 and the container tray 18. As the tines moves into the tray tower 11 in the direction of arrow 111, the tray cover lifts slightly as shown in FIG. 12 and the spring 108 is compressed.

Figure 13:
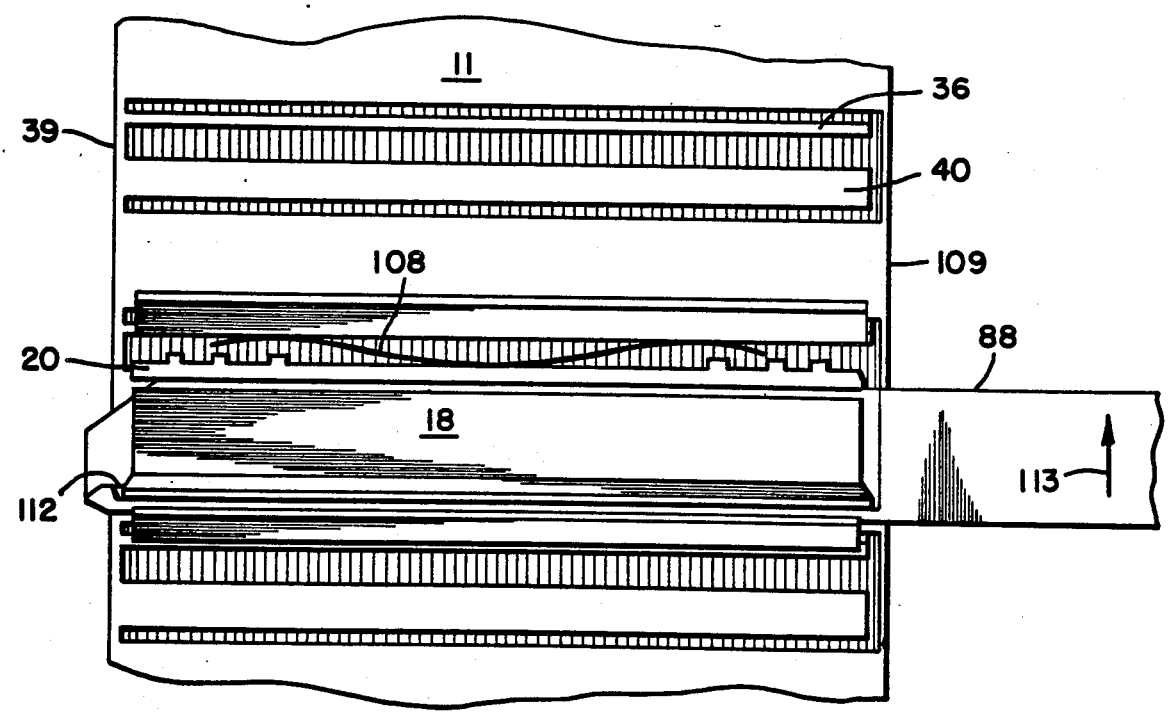
FIG. 13 is a partial side view as in FIG. 11 at a still later stage in the tray moving operation.
Figure 14:
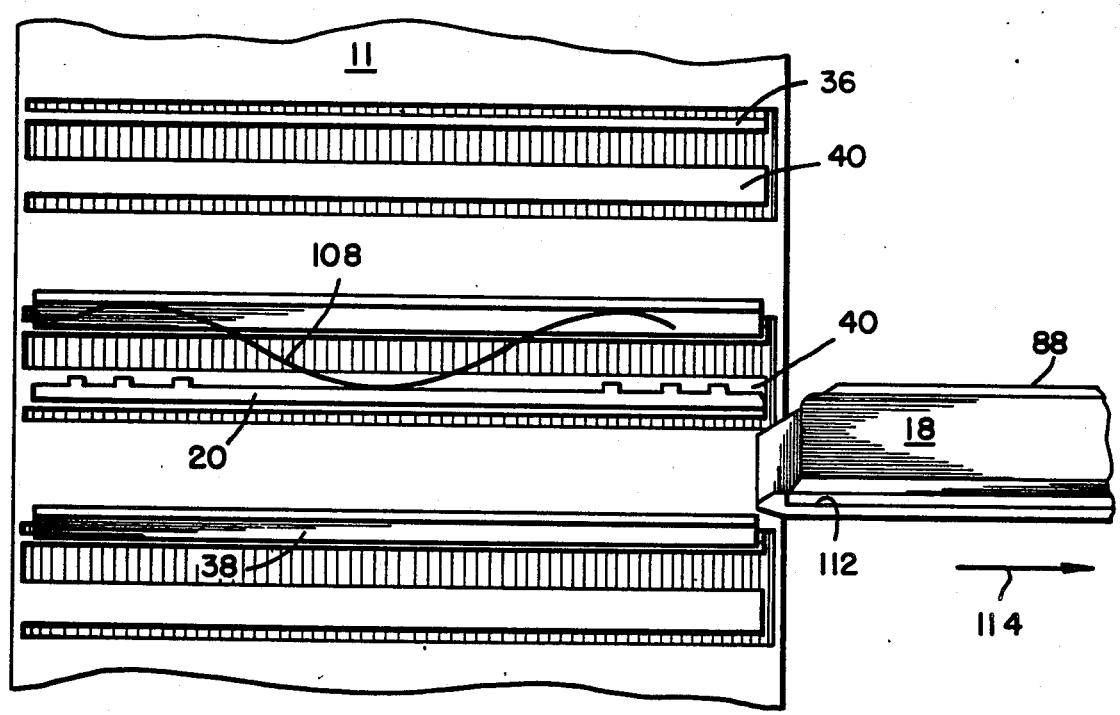
FIG. 14 is a partial side view as in FIG. 11 at a still later stage of the tray moving operation.

Referring now to FIG. 13, after the tines 88 and 89 are fully advanced into the tray tower, the vertical drive stepping motor 66 is actuated to slightly raise the tines 88 and 89. This causes the tray cover 20 to be fully lifted off the container tray 18 and held in that position by the tray tine 88 and the opposing tray tine 89 not shown. This also serves to capture the container tray 18 in a recess 112 in the lower edge of the tines 88 and 89. The spring 108 is now fully compressed. The slight vertical jog in the direction of arrow 113 is all that is necessary in order to capture the container tray 18 in the recess or pocket 112. The container tray is then withdrawn from the tray tower 11 by movement of the tines 88 and 89 in the direction of arrow 114 as shown in FIG. 14. Upon withdrawal of the container tray 18 from the tray tower 11, the biasing spring 108 returns the tray cover 20 to its normal position at the bottom of the second slot 40. The tray cover member 20 does not follow the tines 88 and 89 out of the tray tower because of the closed end 109 of the second slot 40 which captures the tab portion of the tray cover member 20.

To return the container tray 18 to the tray tower 11, the operation is reversed. As the tines 88 and 89 advance into the tray tower 11, and tray cover member 20 is raised up to permit the tray container 18 to enter. After the tines are fully inserted into the tray tower 11, the stepper motor 66 is jogged to move the tines vertically, downwardly, to release the tray container. The tines are then withdrawn from the tray tower. The work station can then be advanced up or down to remove another tray from the tray tower.

In operation of the system thus far described, the specimen tray assembly 17 is inserted in the tray tower 11 by the operator. The computer controller 16 controls the actuation of the respective stepper motors previously described to withdraw desired tray assemblies 17 one at a time from a tray tower and transport them to the work station 12. At an appropriate time a tray assembly 17 is withdrawn from the tray tower, it is intended to dispense suitable reagents into the specimens in the tray container. This reagent dispensing process is accomplished by utilizing the respective X axis and Y axis movements achievable through the use of the tray moving system and the remote dispense head moving system. For example, X movement can be achieved by appropriately controlling stepper motor 93 to stepwise advance the tray container supported in the tines 88 and 89 under the dispensing head 15. Y movement is achieved by stepwise advancing the dispensing head from side-to-side of the carrier frame 58 under the actuation of stepper motor 79. The computer controller 16 controls the respective actuations of the stepper motors to move the dispensing head to the desired cuvette 19 in the tray container 18 wherein a desired reagent is then metered therein.

The dispensing head 15 also includes a reader means R for reading the bar code 32 on the side 29 of the container tray 18. This is achieved by scanning the dispensing head 15 laterally across the bar reading means R. The reading means R comprises a sensor on the remote dispensing head for reading the bar code and is appropriately connected to the control system 16 to identify the sample being analyzed.

After reagent dispensing is completed by the respective X and Y axis movements of the respective tray moving system 13 and movement of the dispensing head 15, the stepper motor 93 is energized to advance the tines in a direction to reinsert the container tray 18 back into its respective slot in the tray tower 11 as described by reference to FIGS. 10–14. The computer controller 16 then allows the inoculated samples with added reagents to incubate a desired amount of time after which the container tray 18 is again removed from the tower by repeating the sequence described by reference to FIGS. 10–14 and withdrawn to the work station 12.

At this time, the analysis is carried out in a manner similar to that described for the MicroScan system in the background of this application. When the container tray is in the work station 12, the respective tray block, aperture plate and optics block frame are moved into engagement with the bottom of the container tray 18 by means of actuating stepper motor 106. After the analysis has been completed in a conventional fashion and the results recorded in the computer controller 16, the tray block, is lowered by actuation of stepper motor 106 and the tray tines again return the tray container to the tray tower. At this point, the tray container may be removed for storage or disposal as desired. In the alternative, it may be retained in the tray tower for an additional incubation period if so desired and the analyzing operation just described repeated following the incubation period.

It has previously been described that the tray cover member 20 includes a recess 26 defining an inclined peripheral wall 28 which serves to center the container tray relative to the cover member. This action is achieved as shown by reference to FIGS. 10-14 under the influence of the biasing spring 108. If the tray container 18 should be reinserted in the tower 11 in slight misalignment from the cover member 20, then the cover member 20 can properly align it. This is possible since as the cover member 20 is engaged to the container tray 18 as the tines 88 and 89 are withdrawn, the inclined surface 28 serves to move the container tray relative to the cover member which is held from moving by the sidewalls in order to center the container tray and provide good sealing engagement between the cover member and the container tray.

The incubation in the apparatus of this invention is preferably carried out at about 37 degrees C, plus or minus 3 degrees. Since different tests require different incubation times, the computer controller 16 is set up so that each tray assembly 17 will be read based upon the tests which are desired for the specimens in that respective container tray 18. The apparatus 10 of this invention is designed to read trays which have differing tests as the analysis functions, reagent dispensing functions and incubation periods are software determined. It is possible with the apparatus 10 of this invention to do kinetic readings as the various readings can be taken over a period of time thereby providing rate of growth studies in any particular cuvette 19.

The reader assembly for analysis includes a light source assembly comprising ninety-six fiber-optic lines from a light source. Each fiber-optic line is provided under each well in the tray. Over the tray, an aperture plate, or merely the light sensor, is used. The light is provided by a light source which is separated from the end of the fiber-optic bundle by an appropriate color wheel which provides filtering of the light due to various tests. Preferably, the color wheel includes nine colors, although normally only seven colors are read. The color wheel and light source assembly, as previously described, is essentially of the type previously employed with the auto SCAN system described in the background of this application. All seven readings are taken for each cuvette 19 and the associated software of the controller 16 throws out any unnecessary readings for each well. After a particular tray 18 has been read to completion, a light emitting diode D on the housing H will either be lighted or turned off to indicate that the tray has been analyzed and can be removed or replaced with another tray.

Figure 15:
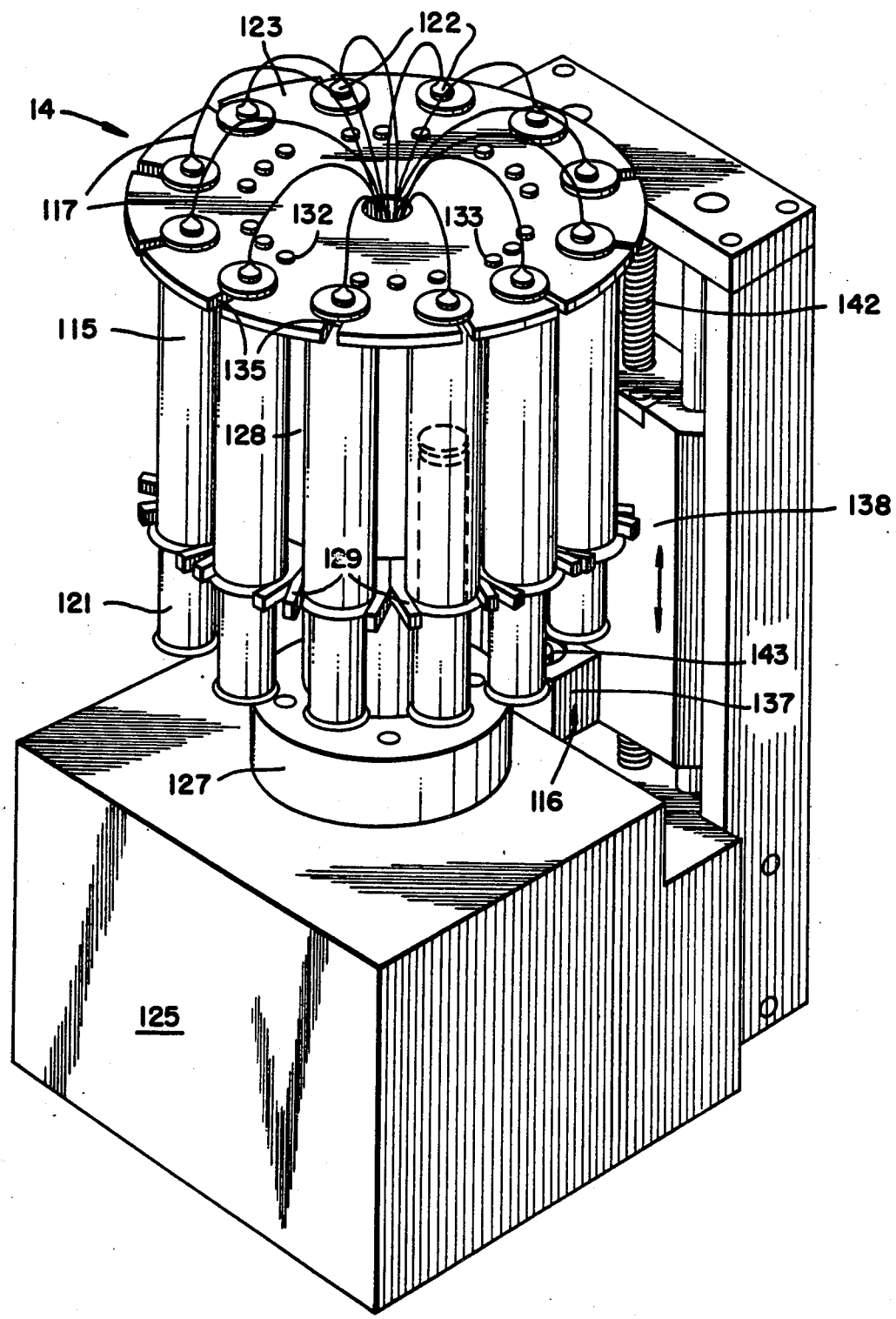
FIG. 15 is a perspective view of the dispenser systems.
Figure 16:
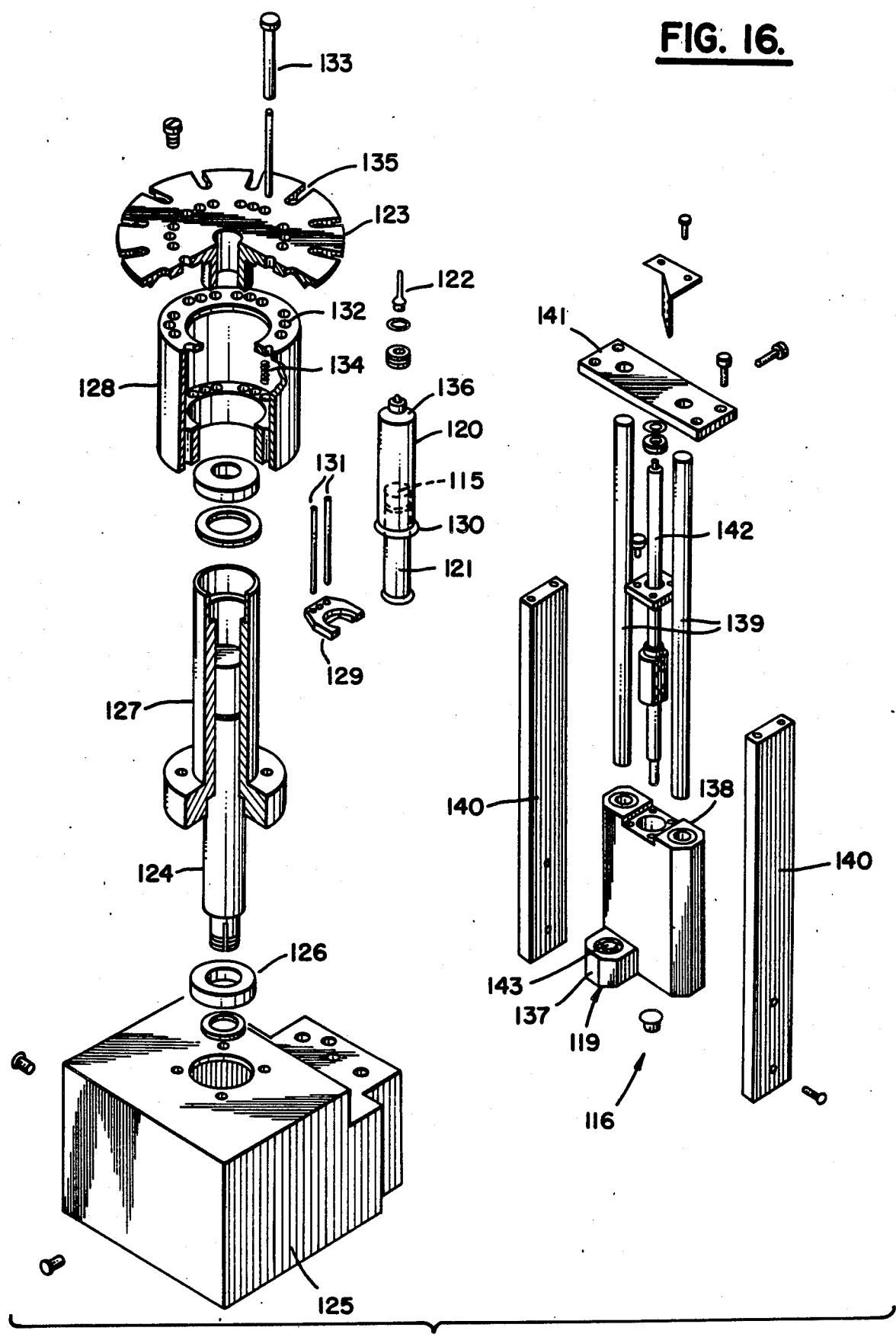
FIG. 16 is an exploded view of the dispenser system of this invention.

While the operation of the remote dispensing head 15 has been described in detail, reference will now be had to FIGS. 15 and 16 wherein the reagent delivery system 14 is shown in detail. The reagent delivery system 14 comprises a plurality of reagent supply containers 115 arranged remotely from the work station 12 and means for selectively dispensing a desired amount of a reagent from a corresponding one of the reagent supply containers 115. A suitable conduit 117, as shown in FIG. 1, connects each respective container 115 to a respective dispensing hole 118 in the dispensing head 15 shown in FIG. 9. Accordingly, there are as many conduits 117 and dispensing holes 118 employed as their are containers 115 mounted in the delivery system 14.

The selective dispensing means comprises a dispensing station 116 in which the reagent containers 115 are arranged for movement past the dispensing station. Metering means are provided at the dispensing station for controlling the amount of reagent dispensed from the reagent container 115 selected. Preferably, the reagent containers 115 comprise syringes comprising a container body 120 and plunger 121. A suitable syringe nozzle 122 is used to connect the syringe 115 to the conduit 117.

It is preferable, in accordance with this invention, to move the syringes past the dispensing station 116 by supporting the syringes in a carousel 123 arranged to rotate the syringes past the dispensing station 116. Means are provided for selectively moving the carousel 123 to position a desired one of the syringes 115 at the dispensing station 116. The carousel 123 is mounted to shaft 124 which is journaled for rotation in a support base 125 by means of bearings 126. A stepping motor (not shown) in the base 125 is drivingly connected to the shaft 124 and, under the influence of control system 16, stepwise advances the carousel 123 to position a desired one of the containers 115 at the dispensing station 116. The control system 16 not only coordinates the movement of a desired one of the reagent containers to the dispensing station 116, but also controls the amount of reagent metered therefrom at the dispensing station in correspondence with the specimen arranged to receive the reagent.

The syringes 115 are releasably supported in carousel 123. This is achieved by providing a dispenser body housing support collar 127 about shaft 124 and a dispenser body housing 128 fitted over the collar 127. The carousel 123 is then supported on the end of shaft 124. A movable syringe mounting block 129 is arranged to support the syringe by engaging a flange 130 of the syringe container body 120 from below. The mounting block 129 is mounted on two dowel pins 131 arranged parallel to one another and arranged for sliding movement in holes 132 in the dispenser body housing 128. A syringe release shaft 133 is also slidingly mounted in housing 128 so as to be spring biased by a spring 134 in an upward direction. The lower end of the shaft 133 is secured to mounting block 129.

The carousel 123 includes a series of slots 135 about its periphery through which the nozzle 122 of the syringe can pass, however, the shoulder 136 of the syringe abuts against the carousel plate from below. Therefore, in operation, to insert the syringe in the carousel assembly, the shaft 133 is depressed to lower the mounting block 129. The syringe 115 is then inserted so that the nozzle 122 protrudes through a slot 135 and the shaft 133 is then released so that under spring biasing, the block 129 engages the flange 130 to securely mount the syringe in the carousel assembly by spring biasing it between the mounting block 129 and the carousel plate 123.

The carousel plate 123, depending on its size, can include any desired number of syringes. A metering means 119 is arranged at the dispensing station 116 which itself is positioned tangentially of the carousel 123. The metering means 119 comprises an anvil 137 arranged for movement longitudinally of the desired one of the syringes at the dispensing station 116. The anvil is supported on a movable carriage 138. The carriage is arranged for movement in a sliding fashion along vertical shafts 139 which are supported at one end in the base 125 and at an opposing end in a frame secured to the base and comprising side bars 140 and top bar 141. Sleeve or linear bearings are used to mount the carriage 138 to the shafts 139.

A drive screw 142 is journaled for rotation in the top bar 141 and extends through the base 125 wherein it is also journaled for rotation. The drive screw is drivingly connected to a stepping motor (not shown) which serves, by virtue of the driving connection between the drive screw and the carriage 138, to move the carriage 138 and the anvil 137 to and fro in a vertical direction; namely, vertically upwardly or downwardly as controlled by the control system. By moving the anvil longitudinally of the syringe 115, it is possible to push the plunger 121 into the body 120 in order to dispense the desired amount of reagent.

The control system 16 controls the stepping motor connected to the drive screw 142, to drive the anvil 138 between respective positions. These comprise a first home position wherein it does not engage the syringe at all, a second dispense start position wherein it first engages the plunger 121 and a third finish position wherein it pushes the plunger into the body 120 to dispense the desired amount of reagent. The control system 16 coordinates the movement of the carousel 123 to position the desired one of the syringes at the dispensing station and also controls via the stepping motor (not shown), the movement of the anvil 138 between its respective positions to dispense the desired amount of reagent. The control system 16 includes a position sensor 143 for sensing the first engagement between the anvil and the plunger 121 and for causing responsive thereto the anvil to move to its third position. In this embodiment, the carousel plate 123 is adapted to rotate just under 360 degrees in either direction in aligning the reagent containers relative to the dispensing station. Each syringe position is coded as well as the home position. In searching for a particular syringe, the sensor is activated by the slots 135 and the computer can identify which syringe is at the dispensing station. If a particular syringe is not placed at the dispensing station before the sensor reaches the home slot the carousel is reversed in direction until it finds the particular syringe.

The apparatus in accordance with this invention is adapted to load and unload a tray container 18 from a tray tower 11 in approximately seven seconds, and a similar amount of time is required to analyze the specimens in the tray. The apparatus, in addition to the position sensor 143 can include a number of other sensing and encoding devices for enabling the control system to control the operation as previously described. For example, encoders are used on the X and Y axes drives during the dispensing operation. Various optical interrupter type sensors are employed for detecting the container tray edge, the tine home position, the dispenser head home position, etc.

It is preferred, in accordance with this invention, as shown in FIG. 8A, to employ roller bearings B supported by frame 98 against which the tines 88 and 89 ride when extending to take the tray from the tray tower 11. This helps to improve the stability of the tray moving system.

The control system 16 has not been described in detail but preferably comprises a programmable computer controller as are well known in the art. It is believed to be well within the skill of the art to program such a device to perform the desired sequences as described.

The patents, patent applications and publications referred to in the background of this application are intended to be incorporated by reference herein.

It should be understood that the above described embodiments of the invention are illustrative only and that modifications thereof may occur to those skilled in the art. Accordingly, this invention is not to be regarded as limited to the embodiments disclosed herein but is to be limited only as defined by the appended claims.

I claim:

1. A reagent dispenser assembly for use in an automated analysis system, said dispenser comprising:

a dispensing station;

a plurality of reagent supply containers associated with said dispensing station;

means for positioning a desired one of said reagent containers at said dispensing station for dispensing a desired amount of reagent therefrom;

means acting on said desired one of said containers at said dispensing station for dispensing therefrom a desired amount of reagent, said dispensing means comprising a plurality of plungers, with each respective plunger being associated with a respective reagent container, the position of each plunger relative to its associated container being determined by the amount of reagent remaining in its container;

a means separate from said containers and plungers for moving said plunger associated with said one of said containers to dispense said desired amount of reagent irrespective of the position of the plunger of said one of said containers prior to said reagent being dispensed, said means for moving said plunger associated with said one of said containers comprises an anvil for engaging said plunger, said anvil being arranged for movement longitudinally of said desired one of said reagent containers, a means for driving said anvil to move it selectively between a first home position where it does not engage said plunger, a second dispense start position where it first engages said plunger and a third finish position where it pushes the plunger in order to dispense said desired amount of reagent; and control means for coordinating the movement of said anvil between its respective positions to dispense said desired amount of said reagent, said control means including means for sensing the first engagement between said anvil and said plunger and responsive thereto, said control means causes said anvil to move to its third position whereby the amount of reagent dispensed is a function of the movement of said anvil between the second dispense start position, which is determined by said means for sensing the first engagement, and said third position.

2. A dispenser as in claim 1 wherein said positioning means comprises a reagent container support carousel arranged to rotate said containers past said dispensing station which is arranged tangentially of said carousel and means are provided for releasably securing said containers to said carousel.

3. A dispenser as in claim 2 further including a dispense head arranged remotely from said dispenser, said dispense head being arranged to administer said reagent to a desired specimen and conduit means connecting said dispense head to said dispenser.

4. A dispenser as in claim 2 wherein said reagent containers comprise syringes and wherein said control means is provided for also coordinating the movement of said carousel to position said desired one of said syringes at said dispensing station.

5. A dispenser as in claim 4 wherein said support carousel includes means for coding the position of each respective syringe as well as a home position and wherein said control means includes means for sensing each of said coded positions and said home position so that said control means can identify which syringe is at said dispensing station and wherein said control means is adapted to reverse the direction in which said carousel is advanced in response to sensing said home position.

6. A dispenser as in claim 5 wherein said coding means comprises slots in said carousel means.

7. A dispenser as in claim 3 wherein said dispense head includes a plurality of dispensing holes with at least one dispensing hole for each of said reagent containers and wherein said conduit means comprises a separate conduit connecting each respective reagent container to a respective dispensing hole in said dispensing head whereby reagent from one reagent container is not mixed from reagent from another reagent container at said dispense head.

8. A dispenser as in claim 7 wherein said positioning means comprises a reagent container support carousel arranged to rotate said containers past said dispensing station which is arranged tangentially of said carousel and means are provided for releasably securing said containers to said carousel.

9. A dispenser as in claim 8 wherein said carousel means is adapted to rotate less than 360° and wherein said carousel means has a home position and wherein said control means reverses the direction of said carousel means upon the sensing of said home position.

* * * * *